United States Patent [19]

Cavanagh

[11] Patent Number: 4,771,394
[45] Date of Patent: Sep. 13, 1988

[54] COMPUTER SHOE SYSTEM AND SHOE FOR USE THEREWITH

[75] Inventor: Peter R. Cavanagh, State College, Pa.

[73] Assignee: Puma Aktiengesellschaft Rudolf Dassler Sport, Herzogenaurach, Fed. Rep. of Germany

[21] Appl. No.: 825,646

[22] Filed: Feb. 3, 1986

[51] Int. Cl.$^4$ .......................... G01C 22/00; A43B 5/00
[52] U.S. Cl. .................................. 364/561; 364/410; 36/132; 36/136; 235/105; 340/323 R
[58] Field of Search ............... 364/561, 565, 410, 413; 235/105; 36/136, 1, 44, 72 B, 132; 324/171, 168; 340/323 R; 272/69, 70

[56] References Cited

U.S. PATENT DOCUMENTS

| | | | |
|---|---|---|---|
| 3,780,272 | 12/1973 | Rohner | 364/561 |
| 4,466,204 | 8/1984 | Wu | 36/136 |
| 4,578,769 | 3/1986 | Frederick | 364/565 |
| 4,649,552 | 3/1987 | Yukawa | 235/105 |
| 4,703,445 | 10/1987 | Dassler | 364/410 |

FOREIGN PATENT DOCUMENTS 3308431 9/1984 Fed. Rep. of Germany ...... 235/105

OTHER PUBLICATIONS

"Gait Analysis Instrumentation", from B & L Engineering, Santa Fe-Springs, Colorado 90670 (date unknown).

Primary Examiner—Parshotam S. Lall
Assistant Examiner—David C. Goldman
Attorney, Agent, or Firm—Sixbey, Friedman, Leedom & Ferguson

[57] ABSTRACT

A pair of running shoes provided with a housing at the heel thereof, into one of which an electronic device is removably mounted. The electronic device comprises a normally open inertia switch for producing a footstrike count, an oscillator crystal for providing a stopwatch function, a sound generating device, a battery power source and a gate array for counting time and footstrikes. The electronic device together with a computer and a cable for enabling communication between the computer and the electronic device in the shoe form a computer shoe system for enabling accurate information to be obtained with respect to a period of usage of the shoes of one or more users as well as enabling a running log to be maintained. The computer shoe system is capable of producing more accurate data related to distance and speed of travel than simple pedometer arrangements because, instead of utilizing a stride length constant, the system converts running time and footstrike data into distance and running speed information as a function of stride time. In a preferred form, the housing for each shoe wraps around the heel thereof so as to form an external heel counter.

6 Claims, 2 Drawing Sheets

COMPUTER SHOE SYSTEM AND SHOE FOR USE THEREWITH

BACKGROUND OF THE INVENTION

1. Field of the Invention

The present invention relates to shoes, particularly running shoes, of the type which provide at least a pedometer function, especially by electronic means.

2. Background Art

Pedometers of various forms have long been known and U.S. Pat. No. 4,402,147 to Wu, for example, discloses a running shoe having a switch embedded in the sole thereof whose output feeds a signal to an electronic step counter. A display element is associated with the electronic counter for providing a digital readout of the number of steps taken with the shoe. However, for a runner to determine useful information from a mere step count readout is complicated, time consuming and inaccurate, even under the best of circumstances.

Johnson U.S. Pat. No. 4,510,704 also discloses a shoe incorporating an electronic pedometer and further discloses that, by incorporating a microprocessor into the pedometer unit, the step count can be converted into values corresponding to such data as the total number of steps taken, distance covered, average speed, peak speed or the like for selective readout by the user on a display incorporated into the device. However, the unit of this patent is basically merely a combination pedometer and stop watch with means to calculate distance and time related data on the basis of a constant that corresponds to an average stride length that is set by the user in a memory storage location of the processing circuitry.

While such a device enables a user to obtain time and distance related data in a less complicated and cumbersome manner that can be achieved via a mere pedometer and stop watch, the resulting data is no more accurate due to the crude calibration of the processor unit that unrealistically relies upon a single average stride length that is the same for all speeds at which the shoe wearer travels. In this regard, Searcy, in his disclosure relative to a jogger's computational device in U.S. Pat. No. 4,220,996, points out that conventional mechanical or electronic pedometers are not useful for providing an indication of distance traveled since the normal length of stride varies depending upon whether the athlete is walking, jogging or running; although, despite this recognition, the calculations performed by Searcy's computational device still are determined on the basis of a single, average stride length approximation that the user inputs, prior to use, on the basis of whether his activity will be running, walking, or jogging.

In addition to the above, the Johnson patent also discloses that, by having his pedometer incorporate a micro-processor that senses footstrikes via a gravitationally or inertially-operated switch or other sensor, no sensor need be incorporated into the shoe itself, so that the unit could be formed as an attachment secured to the shoe, such as by being detachably secured or clipped to the heel thereof, or by being fastened on top of the shoe by a strap. However, no specific manners for implementation of this concept are illustrated or described. Thus, there is no recognition of the problem that could result if such an attachment were not secured firmly enough to the shoe to prevent relative accelerations between the shoe and attachment which could effect operation thereof, nor is there any indication as to how such an attachment could be optimally configured and constructed from both a manufacturing and use standpoint.

Furthermore, a sophisticated running shoe system is disclosed in commonly owned U.S. patent Ser. No. 701,194 filed Feb. 23, 1985, that enables distance-related data to be accurately produced. However, the system of this application achieves such accuracy by measurement of actual stride length and requires a transmitter-receiver arrangement capable of providing signal inputs from which actual stride length determinations can be made.

Thus, no simple pedometer-type shoe arrangement exists which is capable of producing accurate data related to the distance and speed of travel of a user thereof. Likewise, no attempt has been made, until now, to provide a shoe system which will not only provide accurate data, but which can form part of a comprehensive record keeping and training system which is adapted, not only to the use of a particular individual, but also to the needs of organizations such as running clubs, track teams, and the like. In particular, there has been no attempt to provide a shoe with an electric device capable of communicating with a computer in order to take advantage of the fact that personal computers are now in relatively widespread use as a convenient and accurate means of keeping records, so as to integrate the shoe system into a comprehensive record keeping and training analysis system.

SUMMARY OF THE INVENTION

In view of the foregoing, it is an object of the present invention to provide a simple and versatile running shoe system that will provide accurate data concerning the activities of one of more shoe wearers.

It is another object of the present invention to provide a running shoe having an electronic device capable of communicating with a computer.

It is still another object of the present invention to provide a running shoe with an electronic device, the electronics of which are housed in a manner that enables the entirety thereof to be transferred from one shoe to another having a compatible housing for use therein.

Yet a further object in accordance with the present invention is to provide an electronic device, in accordance with the preceding objects, wherein the housing thereof actually contributes to the performance of the shoe as a running shoe.

These and other objects are achieved in accordance with a preferred embodiment of the present invention wherein one, and preferably both of a pair of running shoes is provided with a housing at the heel thereof, into one of which an electronic device is removably mounted. The shoe mounted electronic device comprises a normally open inertia switch for producing a footstrike count, an oscillator crystal for providing a stopwatch function, a buzzer or other sound generating device for providing acoustic indications to the user, a battery as a power source and, most importantly, a gate array including a pair of dividers, one for time in seconds and one for footstrikes.

External aspects of the system include a personal computer and a cable for coupling the computer to the shoe electronics. The computer enables a running log to be maintained for an unlimited number of electronic shoe users, the information stored within the shoe as a result of a period of usage to be decoded, and information to be down-loaded into the shoe when, instead of recording information concerning a run to be made, it is desired to set a goal for the run and have the shoe produce an appropriate acoustical indication when such is achieved.

Because the electronic device in the shoe provides the footstrike count and the run time, but a separate processor unit assimilates this information into meaningful data, the shoe electronics can be kept relatively simple, yet a single system can be utilized by a number of runners and can accurately provide a large range of distance and time related information as well as caloric expenditure, including graphic displays of goals verses actual distances. In this regard, despite the simple electronics carried by the shoe, a high degree of accuracy is achieved, in comparison to that achieved by existing pedometer type devices, due to the fact that the system does not rely on a single preset average stride length value for calculating the output values, such as distance covered, average speed, and the like. Instead, the system of the present invention determines a pair of stride length regression constants for use in the calculation of the desired information from data values obtained during a usage period so as to take advantage of the knowledge that stride length and stride time vary considerably as a function of running or walking speed and, thus, a more accurate determination can be made if it is known how fast the user was actually traveling.

In particular, the system in accordance with the present invention is not calibrated by the use of a predetermined average stride length, but rather is calibrated through the inputting of a plurality of times and numbers of footstrikes at which a predetermined distance was covered (for example, data from ten to twenty calibration runs must be input). From this information, the computer is able to produce a regression line to describe the individual footstrike time-speed relationship for each user. Thereafter, distance, time and caloric cost information can be calculated for any given run based upon the user's body weight and stride time regression relationship read from computer memory and run data read from the shoe.

Similarly, for preloading the shoe with values so that the shoe will emit tones which, for example, indicate when a given distance has been completed, since one cannot know, in advance, how fast the runner will actually run, the invention does not merely load a number of footstrikes into the shoe electronics that is equal to the desired distance divided by some predetermined average stride length. Instead, the present invention is able to examine the speed used over a preceding period of time (such as the last 30 days) for which data exists. Then the mean of these values can be taken and the stride time for this speed calculated from the regression coefficients, thereby enabling the number of strides at this speed that would be needed to travel the required distance to be determined and loaded into the shoe electronics.

In order to enable an electronic device capable of communicating with a computer to be incorporated into a running shoe, not only without detracting from the performance characteristics of the shoe, but in a manner complementing it, the housing for the shoe electronics, in the preferred embodiment, has been shaped to be secured about the heel of the shoe in the form of an external counter. Thus, the housing enables the known benefits of an external shoe counter support to be obtained in an effective manner, but without such having to be incorporated during manufacture of the shoe proper. In this respect, it is noted that both shoes of a pair have such housings, even though only one housing will actually receive the electronic device and the other will be merely a dummy housing. In a related vane, it is noted that the present invention, with the provision of dummy housings for the shoe electronics, makes it unnecessary for a person to buy the electronics more than once since, after the original pair of shoes has worn out, subsequent pairs having only dummy housings can be purchased and the electronic device from the worn-out pair simply transferred into one of the dummy housings of the new pair.

These and other features and advantages of the present invention will become apparent to those of ordinary skill in the art from the following description and accompanying drawings which describe, for purposes of illustration only, a preferred embodiment of the present invention.

DETAILED DESCRIPTION OF THE PREFERRED EMBODIMENT

Figure 1:
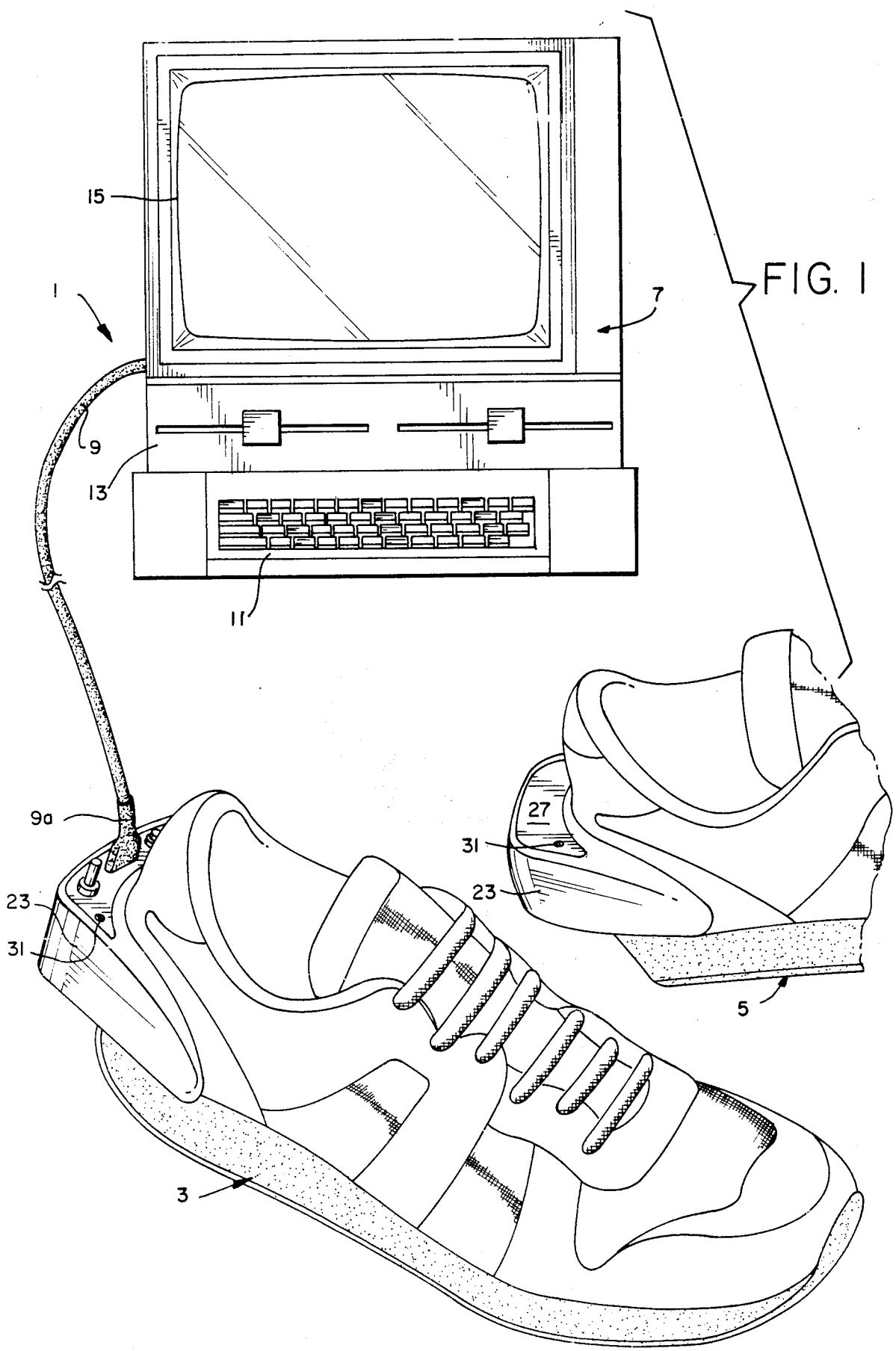
FIG. 1 is a partial perspective view of a preferred embodiment computer shoe system in accordance with the present invention.
Figure 2:
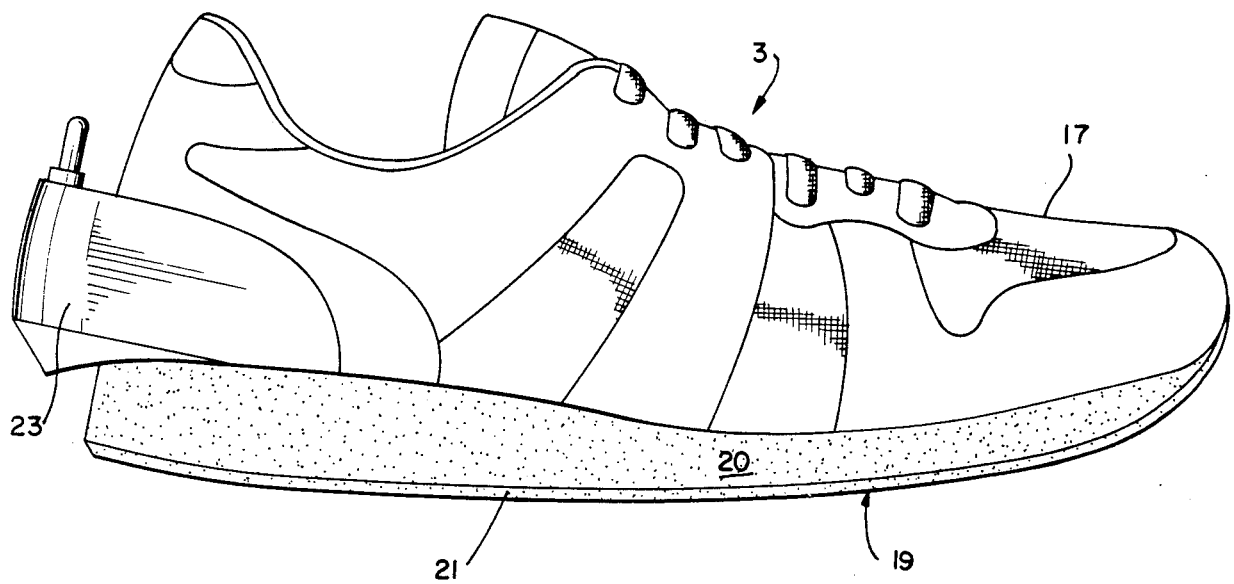
FIG. 2 is a side elevational view of a shoe forming part of the computer shoe system of the preferred embodiment.

In FIG. 1, a complete running shoe system, in accordance with a preferred embodiment of the present invention, is designated generally by the reference numeral 1. This system is comprised of a pair of running shoes 3, 5, a computer (such as a personal computer, for example, an "Apple IIe" personal computer) and a detachable cable 9 by which an electronic device carried by one of the shoes 3, 5 may communicate with the computer 7 before and/or after a usage of the shoes. As typical of such personal computers, it includes a keyboard 11, disk drive 13 and display monitor 15.

The running shoes 3, 5, as is conventional for running shoes, has of an upper 17 and a sole 19 that is comprised of a shock absorbing midsole 20 formed, for example, of a polyurethane foam and an outer sole 21 of a wear resistant material. Furthermore, no special modifications need be made to these components of the running shoes 3, 5 and thus any known running shoe construction may be utilized, including those provided with anti-pronation inserts and specialized outer sole configurations, and the like.

In addition to the noted conventional components, the running shoes 3, 5, in accordance with the present invention, are provided with a housing 23 that is firmly secured to the heel of each running shoe 3, 5. In this regard, it is known to provide an athletic shoe with an external heel counter to provide good heel stability and comfort while preventing blistering. In accordance with the present invention, the housing 23 has been configured so as to provide the characteristics of such an external heel counter by being attached to the exterior of the heel portion of the shoe upper in a manner completely wrapping around the heel from one side to the other and tapering at it front ends.

Figure 3:
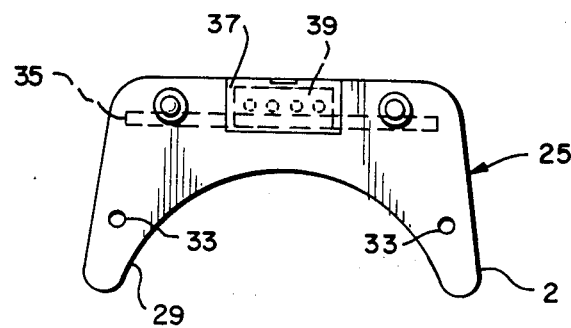
FIG. 3 is a top plan view of the electronic device of the shoe shown in FIG. 2.
Figure 4:
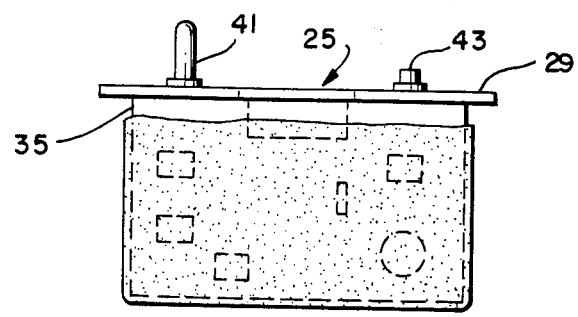
FIG. 4 is a side elevational view of the electronic device of FIG. 3.

However, the primary function of housing 23 is to provide a receiving space for an electronic device 25 (FIGS. 3 and 4) constituting the shoe carried electronics portion of system 1. To this end, housing 23 is formed of a hollow shell of a rigid plastic material having an opening on its top side which may be closed by a plate 27 (when no electronics are provided) or when the electronic device 25 is installed, by a closure plate 29 thereof which is identically shaped to closure plate 27. The plates 27, 29 are held in place so as to sealingly close the top opening of the housing 23 by, for example, a pair of screws 31 which may be passed through openings provided therefor, such as the openings 33 shown in plate 29 in FIG. 3. Furthermore, to provide a receiving space within the housing 23 of sufficient height to accommodate a circuit board 35, projecting vertically from the underside of closure plate 29 of the electronic device 25, without undesirably increasing the size of the housing or affecting the housing's function as an external heel counter, or the running performance of the shoe itself, the bottom side of the housing 23 is provided with a downwardly projecting wedge-shaped area, the apex of which is positionally set so as to be in alignment with the bottom edge of the circuit board 35 of the electronic device 25, when it is installed within the housing 23.

In addition to the cover plate 29 of the circuit board 35, the electronic device 25 that is carried by the shoe is comprised of the following further components. Firstly, cover panel 29 is provided with an integrally hinged access flap 37, which is swung upwardly to enable the connector 9a of the cable 9 to be attached to an electrical connector 39 (FIG. 3) of the electronic device 25, but which will prevent moisture and dirt from entering the housing when the cable 9 is disconnected for use of the shoe for walking, running or jogging. The other two components which would be visible in an installed condition of the electronic device 35, are a toggle switch 41 and a mode selection button 43; although a pair of switches or a pair of buttons, or equivalent means, are equally suitable. Both switch 41 and button 43 are enclosed, at the top side of cover plate 29, by a flexible rubber or plastic jacketing which will protect the toggle switch, mode button and internal electronics from dirt and moisture, yet will not interfere with the movements required for operation thereof.

In addition to the already noted components of the electronic device, the circuit board contains a gate array, an inertia switch, an oscillator crystal, a battery and a sound emitting device. The portion of the circuit board 35 carrying these components and all moisture sensitive parts carried thereon (see FIG. 4 wherein these components are schematically represented in broken lines) are coated with a moisture proofing material, such as a butyl rubber or the like, to further ensure that the device will not be adversely affected by moisture or dirt to which the shoe is exposed during use.

When the toggle switch 41 is shifted from its off position to its on position, the gate array is capable of being placed in any one of three different modes of operation. Firstly, when the electronic device 35 is turned on by shifting the toggle switch 41 from its off position to its on position, the device powers up in a test mode, from which it can be shifted by operation of the mode button 43 into a run mode or into which the gate array will automatically shift, from either the test or run modes, when the device is left undisturbed for more than a predetermined period of time, such as for example, 16 seconds, wherein the oscillator is switched off reducing battery drain to a trickle level. The nature and operation of the test and run modes will be described in greater detail below. Alternatively, turning on of the electronic device 35 can be triggered by an impact to the shoe, via an impact sensitive switch such as the already present inertia switch. In such a case, the switch 41 can serve, instead, as a reset switch for clearing any values stored in the memories of electronic device 35.

An important part of the gate array is a pair of dividers, one for time in seconds and one for foot strikes. When the shoe is in the "run" mode the oscillator advances the counter in the time divider every second and each footstrike is detected by the inertia switch and causes the other divider to be incremented. In the test mode, the two dividers can also be incremented by an external pulse from the computer for reasons which will become apparent later. Inasmuch as a typical stride time is 0.7 seconds, the capacity for the foot strike count divider should be approximately 30% greater than that for the time count in seconds. By way of example, it is noted that a 19 bit divider would overflow after 524,288 pulses have been received (from either internal, external or both sources) and would correspond to over 145 hours of running time, while a 14 bit divider could accumulate 4.55 hours of time and 16384 foot strikes.

In addition to enabling the dividers to be incremented by an external pulse (which enables communication between the computer and the gate array so that the dividers can be interrogated) except for such external signal pulses, the test mode freezes the counts in the dividers, thereby storing the values contained therein so that, for example, the values can be frozen during a brief interruption in a run or between completion of a run and the time at which the data contained therein can be transferred to the computer 7. Furthermore, the test mode can be utilized to enable the user to determine that the electronic device 25 is operating properly by causing a tone to sound every time that the inertia switch closes, i.e., the user, by hitting the shoe once or twice against a hard surface, may verify that the device is working by listening for the production of a tone.

To determine the count stored in the dividers, with the device 25 in its test mode, the dividers are interrogated by the computer delivering signal pulses, via the cable, to the divider and counting the number of pulses delivered until a signal is received from each divider indicating that it has been caused to overflow. When the dividers have overflowed, the count required to overflow each of the time and footstrike dividers is stored in the computer as a value equal to the difference between the count capacity of the divider and the number of counts required to cause it to overflow. At this point calculations by the computer processors can proceed; however, unlike known pedometers, in accordance with the present invention, the data obtained with respect to the number of footstrikes occurring during a usage is not multiplied by a stride length constant to obtain distance. Instead, as will be explained in greater detail, in accordance with the present invention, a much more accurate distance determination is obtained by taking into consideration the fact that an individual's stride pattern varies with speed and is normally unique to that individual.

In particular, the present invention compensates for the fact that stride length varies considerably as a function of running or walking speed by utilizing the fact that stride time, i.e., the time between two successive strikes of the foot, is also a function of speed. For example, a typical stride time of approximately 0.73 seconds could be expected at a speed of three meters per second, which stride time might change to approximately 0.70 seconds at a speed of four meters per second.

As a result, the system of the present invention provides a means for each user to enter calibration data corresponding to the number of footstrikes and the elapsed time taken to cover a fixed distance course. In order to obtain accurate calibration, these data pairs should be obtained from at least 15 runs or walks of varying speeds taken on at least five separate days. Additionally, the system provides means for producing a velocity-stride time regression equation from the calibration data points and for storing these constants for use in evaluating the particular user's future performance with the running shoes of the system. In this regard, it is noted that the relationship between running speed, V, and stride time (which is equal to the elapsed time, T, divided by the number of foot strikes, S, counted) may be expressed by the following equation, wherein A and B are regression coefficients generated from the calibration data:

$$V = A*T/S + B$$

Furthermore, once the running speed has been determined from the stride time, the distance run may be determined from the running speed and running time in accordance with the equation:

$$D = V*T$$

Thus, in accordance with the invention, no matter what speed the user runs or walks with the shoes 3, 5, the system will adjust the data extracted from the electronic device 25 carried by shoe 3 so as to produce running speed and distance information that is much more accurate and useful than that which could be obtained from a mere pedometer because it is based upon stored data reflecting the specific individual's own performance characteristics.

Additionally, to offset errors that occur in measurement that tend to bias the calculations towards a longer predicted stride time than the actual stride time, it is desirable to unbias the extracted data prior to use thereof in the above-noted calculations. In particular, since it takes a runner a finite amount of time to start running after switching on the shoe, and a finite amount of time to turn the shoe off after running, a value of, for example, 3 seconds, should be substracted from the time value extracted from the electronic device 25 and this adjusted time value used instead. Likewise, since it is more likely for the shoe to miss a few foot steps because the runner may occasionally make a light step (which is below the threshold of the inertia switch) than for the electronic device 25 to count too many footstrikes, it is suggested that the number of footstrikes extracted from the shoe electronics 25 be increased by a small fixed percentage by multiplying the count extracted by an unbiasing factor, such as a value of 1.01. Thus, a typical relationship for determination of running speed might be:

$$V = -33.0*(T+3)/(S*1.01) + 27$$

Another advantage of the present system, which utilizes a separate and independent computer, over simple electronic pedometers is the ability to accumulate and plot statistics over a period of time, such as a month, or a year, and to compare it with goals that have been entered into the system. For example, plots of distance by month and by day, can be produced. Additionally, by providing a means for storing user body weight values, output in terms of caloric expenditure resulting from a particular run can be produced as well.

In addition to providing the ability to obtain accurate information concerning a user's performance as well as providing a means for storing and analyzing the performance of one of more user, in accordance with another advantageous feature of the present invention, it is possible to set a distance goal in the shoe electronic device 25 so that a tone will be produced informing the wearer when that distance has been covered. In accordance with the present invention, an approach which may be taken is for the system to examine the running speeds of the user over, for example, the past 30 days, for which data exists in memory, and from the mean of these values to calculate, from the regression coefficients, the stride time for this speed. On this basis, the number of strides which would be required to travel the desired distance at this speed is calculated. The shoe is then reset and the computer 7 operated to pulse the dividers of the gate array of the electronic device 25 so as to bring the divider to within the calculated number of strides from overflowing. Thus, once the required number of footstrikes have occurred with the shoe, the desired distance should have been covered and a tone will sound to so advise the wearer.

From the foregoing, it will be appreciated that the present invention provides a computer shoe system that is more accurate and versatile than any mere pedometer could be, while being simple and easy to use. Furthermore, it will also be appreciated that the design of the shoes of the present system includes a housing that not only is a constructional component for enclosing the on-board electronic device of the shoe, but also improves the stability of the shoe itself.

Additionally, since running shoes have only a finite life, the design by which the housing removably receives the onboard electronics enables the life of the electronic device to extend beyond that of the original shoes. That is, once a first pair of running shoes has worn out, a replacement pair, both shoes of which have dummy housings (as shown for shoe 5) can be acquired, whereby the electronic device 25 can be transferred from the worn-out shoe to one of the replacement shoes. Likewise, this feature affords the possibility that a club or team could have a computer shoe system, with a single computer and one or more electronic devices 25, service a much larger number of runners, each of which has their own pair of shoes 3, 5 to one of which an electronic device 25 can be installed and removed as needed.

While I have shown and described various embodiments in accordance with the present invention, it is understood that the same is not limited thereto, but is susceptible of numerous changes and modifications as known to those skilled in the art. For example, the inventive conversion of footstrike count and time data into running speed and distance information as a function of stride time can be advantageously used in a system that may or may not be able to communicate with a separate and independent computer, e.g., a system wherein electronic device 25 includes a microprocessor, calibrated with the described regression coefficients, and an electronic display, whereby the data from the gate array can be fed to the microprocessor, the above-noted computations performed, and the calculated information on speed and distance provided to the user on the shoe display, virtually immediately, after which the user may or may not electronically communicate the data or information to a separate and distinct computer for graphic analysis, record keeping, etc. I, therefore, do not wish to be limited to the details shown and described herein, but intend to cover all such changes and modifications as are encompassed by the scope of the appended claims.

I claim:

1. A computer shoe system comprising a pair of running shoes, an electronic device that is mountable to at least one of the running shoes and operable to store running time and footstrike count data pertaining to a use of the running shoes by a wearer, and means for enabling communication of said running time and footstrike count data to a separate and independent computer after completion of a usage of the running shoes; wherein said electronic device comprises an inertia switch for producing footstrike indicating signals, a time signal generating means, and a gate array having a respective divider for counting each signal produced by the inertia switch and the time signal generating means; wherein said electronic device, as a whole, is removably mounted within a housing carried by at least one shoe of said pair of shoes; wherein said electronic device comprises cover means for sealing said housing upon mounting of the electronic device therein, wherein operating controls and a connector for a computer connector cable are accessible from an exterior side of said cover, wherein said gate array, inertia switch, time signal generating means and a power source therefor are carried by an interior side thereof; and wherein said housing is configured to form an external heel counter for providing rear foot stability; and a like configured housing and a closure therefor are provided on the other shoe of said pair of shoes.

2. A computer shoe system comprising a pair of running shoes, an electronic device that is mountable to at least one of the running shoes and operable to store running time and footstrike count data pertaining to a use of the running shoes by a wearer, and means for enabling communication of said runner time and footstrike count data to a separate and independent computer after completion of a usage of the running shoes; wherein said electronic device, as a whole, is removably mounted within a housing carried by one shoe of said pair of shoes; wherein said housing is configured to form an external heel counter for providing rear foot stability; and wherein a like configured housing and a closure therefor are provided on the other shoe of said pair of shoes.

3. A running shoe for use in a computer shoe system comprising an upper, a shock-absorbing midsole and a wear resistant outer sole, wherein a housing is affixed to a heel of the shoe in a manner forming an external rearfoot stabilizing counter wrapped around the upper from one side of the heel to an opposite side thereof, said housing having a chamber for receiving an electronic data accumulating device.

4. A running shoe according to claim 3, wherein a removable cover plate is provided for closing an opening of said housing through which the electronic data accumulating device is insertable into said chamber.

5. A running shoe according to claim 4, wherein said cover plate is provided as part of said electronic data accumulating device.

6. A running shoe according to claim 5, wherein said electronic data accumulating device comprises an inertia switch for producing footstrike indicating signals, a time signal generating means, and a gate array having a respective divider for counting each signal produced by the inertia switch and the time signal generating means and is formed as a unit that is removable, as whole, from said housing for reuse in another shoe having a like-constructed housing.

* * * * *